US00PP37563P3

(12) United States Plant Patent
Taerwe

(10) Patent No.: US PP37,563 P3
(45) Date of Patent: Aug. 4, 2026

(54) ***ANTHURIUM* PLANT NAMED 'AA4502'**

(50) Latin Name: ***Anthurium* hybrid Schott**
Varietal Denomination: AA4502

(71) Applicant: Deroose Plants N.V., Evergem (BE)

(72) Inventor: Laurent Taerwe, Gavere (BE)

(73) Assignee: Deroose Plants NV, Evergem (BE)

( * ) Notice: Subject to any disclaimer, the term of this patent is extended or adjusted under 35 U.S.C. 154(b) by 0 days.

(21) Appl. No.: 19/393,361

(22) Filed: Nov. 18, 2025

(65) Prior Publication Data

US 2026/0157245 P1 Jun. 4, 2026

(30) Foreign Application Priority Data

Nov. 29, 2024 (QZ) ..... PBR 2024/2863

(51) Int. Cl.
*A01H 6/00* (2018.01)
*A01H 5/12* (2018.01)

(52) U.S. Cl.
USPC ..... Plt./368
CPC ..... *A01H 6/00* (2018.05); *A01H 5/12* (2013.01)

(58) Field of Classification Search
USPC ..... Plt./368
CPC ..... A01H 6/00; A01H 5/12
See application file for complete search history.

*Primary Examiner* — Keith O. Robinson
(74) *Attorney, Agent, or Firm* — James R. Holm; Plant Novelty Rights, LLC

(57) ABSTRACT

A new and distinct *Anthurium* plant named 'AA4502' particularly distinguished by very dark greyed purple to black coloration of emergent foliage; fast-growing plant, reaching commercial size within approximately 14 months from tissue culture; strong foliage texture, with thick, leathery, and glossy leaves; symmetrical plant habit and vigorous root development; and excellent stability and uniformity in tissue culture propagation.

2 Drawing Sheets

Figure 1:
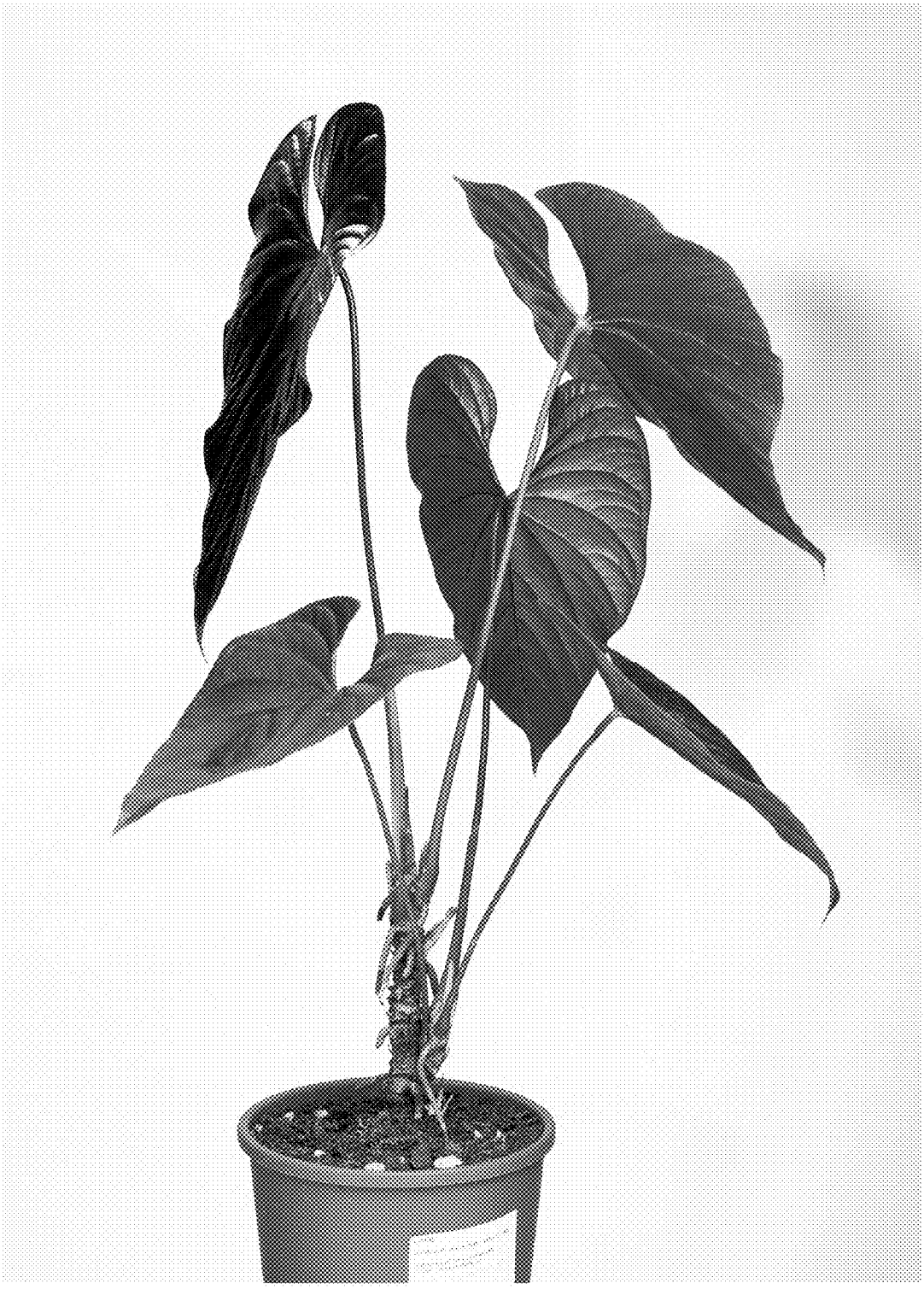

Genus and species: *Anthurium* hybrid Schott.
Variety denomination: 'AA4502'.

STATEMENT REGARDING PRIOR DISCLOSURES BY THE INVENTOR

This application claims priority to CPVO application no. 2024/2863 filed on Nov. 29, 2024, which is herein incorporated by reference. The Applicant asserts that no publications or advertisements relating to sales, offers for sale, or public distribution occurred more than one year prior to the foreign priority date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date.

BACKGROUND OF THE NEW PLANT

The present invention comprises a new and distinct variety of *Anthurium* hybrid Schott., hereinafter referred to by its cultivar name 'AA4502'.

The new *Anthurium* plant is a product of a controlled breeding program conducted by the inventor in Evergem, Belgium. The objective of the breeding program was to create new *Anthurium* hybrids characterized by very dark emergent foliage, rapid vegetative growth, and strong leathery leaf texture. The new *Anthurium* plant originated from a cross-pollination made by the Inventor in September 2019 in Evergem, Belgium between two unpatented and unnamed breeding selections of *Anthurium* hybrids derived from

*Anthurium moodeanum*. 'AA4502' *Anthurium* was selected by the Inventor as a single flowering plant within the progeny of the stated cross-pollination in a controlled greenhouse environment in Evergem, Belgium in 2022.

'AA4502' was first reproduced asexually by meristematic tissue culture in September 2021 in Evergem, Belgium. Asexual reproduction by meristematic tissue culture in a controlled environment has shown that the unique features of the new cultivar are stable and reproduced true-to-type in 5 successive generations.

SUMMARY OF THE INVENTION

The new *Anthurium* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Anthurium* cultivar. The combination of these characteristics distinguishes 'AA4502' as a new and distinct cultivar of *Anthurium:*

1. Very dark greyed purple to black coloration on emergent foliage;
2. Fast-growing plant, reaching commercial size within approximately 14 months from tissue culture;
3. Strong foliage texture, with thick, leathery, and glossy leaves;
4. Symmetrical plant habit and vigorous root development; and 5. Excellent stability and uniformity in tissue culture propagation.

DESCRIPTION OF THE PHOTOGRAPHS

This new *Anthurium* cultivar is illustrated by the accompanying-colored photographs which show the overall appearance and distinct characteristics of the plant. The colors shown are as true as can be reasonably obtained by conventional photographic procedures. The photographs are of 18-month-old plants grown in 12-centimeter circular containers in Evergem Belgium. Colors in the photographs may differ slightly from the color values cited in the botanical description which accurately describes the colors of the new variety.

FIG. 1. shows the overall plant form and foliage of 'AA4502'.

Figure 2:
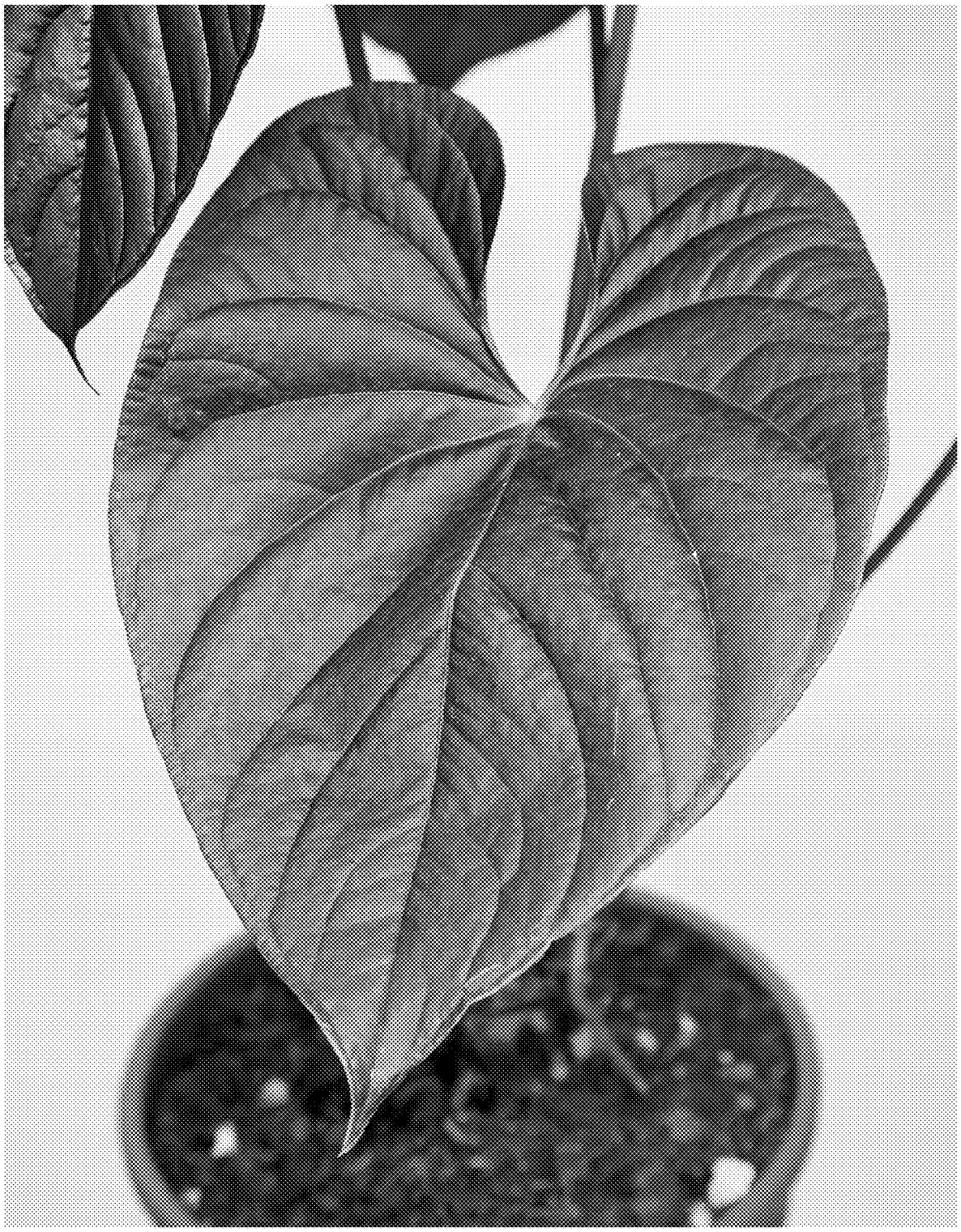

FIG. 2. shows of close up of a mature leaf of 'AA4502'.

DETAILED BOTANICAL DESCRIPTION OF THE PLANT

The following detailed description was taken in November 2025 from 18-month-old plants grown in 12-centimeter circular containers in Evergem Belgium. Measurements and numerical values represent averages of typical plant types. Color references are made to The Royal Horticultural Society Colour Chart, Sixth Edition, except where general color terms of ordinary dictionary significance are used.

Classification:

*Family*.—Araceae.

*Botanical*.—*Anthurium* hybrid Schott.

*Denomination*.—'AA4502'.

General description:

*Plant type*.—Tropical perennial.

*Plant habit*.—Compact, upright and symmetrical.

*Overall plant shape*.—Broad elliptic to obovate.

*Height from soil level to top of foliar plane*.—Approximately 82.0 cm.

*Plant spread or diameter*.—Approximately 64.7 cm.

*Growth rate*.—Moderate.

*Plant vigor*.—Moderate.

*Propagation type*.—Meristematic tissue culture.

*Time required to produce a saleable plant from tissue culture*.—14 months.

*Branching habit*.—Basel branching and lateral branching.

*Stems*.—Quantity: Average two basal stems and one lateral stem. Appearance/shape: Rounded. Length: Basal stem: Average 21.0 cm. Lateral stem: Average 6.5 cm. Diameter: Basal stem: Average 2.6 cm. Lateral stem: Average 1.9 cm. Internode length: Average 1.5 cm. Strength: Strong. Aspect: Main stem near vertical; lateral stems grow at an average angle of 10 degrees from the main stem. Color: Immature: 146A (yellow-green). Mature: Slightly lighter than 199D (grey-brown).

*Roots*.—Moderately fleshy, non-fibrous, colored 179B and 180A (greyed-red), average 30.1 cm in length and 0.3 cm in diameter.

Foliage description:

*Quantity of leaves per stem*.—2.

*Arrangement*.—Alternate.

*Attachment*.—Petiolate.

*Foliage durability to abiotic stresses*.—Moderate to high.

*Lamina*.—Shape: Narrow cordate to cordate. Length: Average 45.2 cm. Width: Average 26.5 cm. Apex: Apiculate with a mucronate tip. Base: Strongly cordate. Margins: Entire, slightly undulate. Texture (both upper and lower surfaces): Glabrous and smooth, moderately leathery. Pubescence: Not present. Venation pattern: Pinnate. Color: Juvenile foliage, upper surface: Interveinal areas: A blend of N186C (greyed-purple) and 203B (black). Primary vein: N186C (greyed-purple). Secondary veins: N186C (greyed-purple). Juvenile foliage, lower surface: Interveinal areas: N199A (greyed-brown). Primary vein: 187B (greyed-purple). Secondary veins: 187B (greyed-purple). Mature foliage, upper surface: Interveinal areas: Darker than near 147A (yellow-green) with a mucronate tip colored 163A (greyed-orange). Primary vein: 146C (yellow-green). Secondary veins: 146C (yellow-green). Mature foliage, lower surface: Interveinal areas: A blend of 146A and 147A (yellow-green) with a mucronate tip colored N144A (yellow-green). Primary vein: N199A (greyed-brown). Secondary veins: N199A (greyed-brown), fading to 187A (greyed-purple) towards the margin.

*Petioles*.—Length: Average 45.5 cm including geniculum. Diameter: Distal end: 1.0 cm. Proximal end: 0.6 cm. Shape: Rounded, upper side flattened. Aspect: Average angle of 30 degrees from stem. Texture and luster: Smooth, glabrous, and moderately glossy. Color: Upper surface: N199A (grey-brown), darkening to NN199B (grey-brown) towards the proximal end and NN137B (green) at the base. Lower surface: N199B (grey-brown), tinged 178A (greyed-red) and NN137B (green) at the base.

*Geniculum*.—Length: Average 3.4 cm. Diameter: Average 0.7 cm. Shape: Rounded, upper side flattened. Aspect: Average angle of 30 degrees from stem. Color: Upper surface: A blend of 152A (yellow-green) and N199A (grey-brown). Lower surface: 178A (greyed-red).

*Petiole wings*.—Length: 4.1 cm. Diameter: 0.6 cm. Color: Upper surface: Slightly transparent 144A (yellow-green), fading to a transparent 144C (yellow-green) towards the edge. Lower surface: 144C (yellow-green).

*Cataphylls*.—General: Young leaves covered by singe cataphyll, folded around leaf and petiole. Shape: Lanceolate. Length: Average 13.7 cm. Width: Average 0.9 cm. Color: 200D (brown), fading to 178A (greyed-red) towards the tip, tip of primary vein and mucronate tip colored 144A (yellow-green).

Inflorescence: None observed to date.

Fruit and seed set: None observed to date.

USDA Hardiness zone: Zone 10 and up.

Disease and pest tolerance: No claims are made to any superior disease or insect resistance or tolerance.

COMPARISON WITH PARENT PLANTS

The new *Anthurium* cultivar 'AA4502' can be distinguished from its female or seed parent in the following characteristics described in Table 1 below.

TABLE 1

| Characteristic | 'AA4502' | Female Parent |
|---|---|---|
| Growth rate | Fast | Moderate |
| Emergent leaf color | Very dark almost black | Medium green |
| Leaf thickness | Thick and leathery | Soft and thinner |
| Leaf glossiness | Very glossy | Matte |
| Petiole color | Dark reddish-brown | Green |
| Plant vigor | High | Moderate |

The new *Anthurium* cultivar 'AA4502' can be distinguished from its male or pollen parent in the following characteristics described in Table 2 below.

TABLE 2

| Characteristic | 'AA4502' | Male Parent |
|---|---|---|
| Growth habit | Compact, upright and symmetrical | Upright but less uniform |
| Emergent leaf color | Very dark almost black | Olive-green |
| Leaf thickness | Thick and leathery | Medium |
| Growth rate | Fast | Moderate |
| Leaf glossiness | Very glossy | Slightly glossy |
| Plant vigor | High | Medium |

COMPARISON WITH COMMERCIALLY KNOWN VARIETIES

The new *Anthurium* cultivar 'AA4502' can be distinguished from the related known commercial *Anthurium* species *A. moodeanum* (unnamed and unpatented) in the following characteristics described in Table 3 below.

TABLE 3

| Characteristic | 'AA4502' | *A. moodeanum* |
|---|---|---|
| Growth rate | Fast | Slow to moderate |
| Emergent leaf color | Very dark almost black | Bronze-green |
| Leaf texture | Thick and leathery | Moderate firm |
| Leaf glossiness | Very glossy | Low to medium |
| Petiole color | Dark reddish-brown | Green |
| Growth habit | Compact, upright and symmetrical | Spreading |
| Foliage density | Dense | Moderate |

What is claimed is:

1. A new and distinct variety of *Anthurium* plant named 'AA4502', substantially as illustrated and described herein.

* * * * *